United States Patent [19]

Hohmann

[11] 4,400,357
[45] Aug. 23, 1983

[54] DEVICE FOR STERILIZING MEDICAL AND DENTAL OBJECTS

[75] Inventor: Eugen Hohmann, Bensheim, Fed. Rep. of Germany

[73] Assignee: Siemens Aktiengesellschaft, Berlin & Munich, Fed. Rep. of Germany

[21] Appl. No.: 294,363

[22] Filed: Aug. 19, 1981

[30] Foreign Application Priority Data

Sep. 9, 1980 [DE] Fed. Rep. of Germany ....... 3033855
Apr. 29, 1981 [DE] Fed. Rep. of Germany ..... 81103233

[51] Int. Cl.³ .......................... A61L 2/08; A61L 2/20
[52] U.S. Cl. ..................................... 422/297; 422/299; 422/300; 422/305
[58] Field of Search ............... 422/297, 298, 299, 300, 422/305, 21, 22, 33

[56] References Cited

U.S. PATENT DOCUMENTS 3,676,058 7/1972 Gray ..................................... 422/21
3,753,651 8/1973 Boucher ............................... 422/21
4,362,241 12/1982 Williams .............................. 422/300

*Primary Examiner*—Richard V. Fisher
*Attorney, Agent, or Firm*—Hill, Van Santen, Steadman, Chiara & Simpson

[57] ABSTRACT

A device which enables a rapid sterilization of one or more medical and dental objects characterized by a first chamber for containing the objects to be sterilized, a second chamber connected to the first chamber and having a smaller volume than the first chamber for receiving a liquid reaction fluid and positioning the fluid in an area of high energy density from a source of radiation such as infrared radiation or microwave radiation so that the object is vaporized and the vaporized gases of the reaction agent flow into the first chamber to sterilize the objects.

23 Claims, 5 Drawing Figures

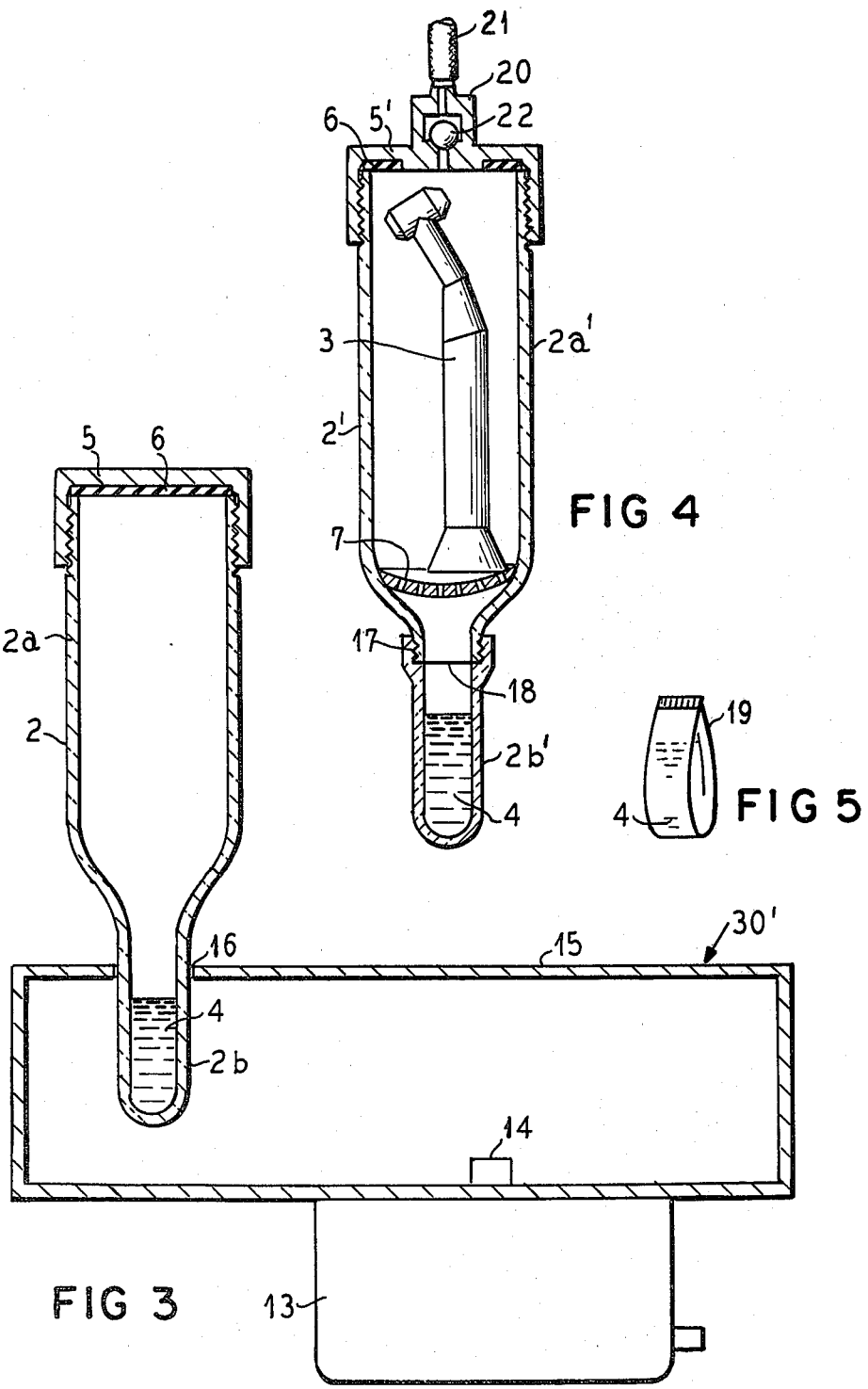

DEVICE FOR STERILIZING MEDICAL AND DENTAL OBJECTS

BACKGROUND OF THE INVENTION

The present invention is directed to a device for sterilizing medical and dental objects for example hand instruments and the like.

Hot steam sterilizers or autoclaves employed in the medical field for sterilizing objects such as hand instruments, tools or the like require relatively long heating and cooling times because among other things they have a relatively great chamber volume. Therefore, the amount of time, which is set aside for sterilization, is inappropriately high. This is particularly true when only a few objects are to be sterilized for example, only the instruments used in one treatment. Moreover, the apparatus structure of an autoclave is relatively involved.

SUMMARY OF THE INVENTION

The present invention is directed to providing a device for sterilizing medical and dental objects such as hand instruments and the like, which device has a simple construction, and can operate with the sterilization time which is signifantly reduced in comparison to traditional devices.

To achieve these objects, the present invention is directed to a device for sterilizing medical and dental objects, such as instruments and the like, by contacting an object with a gas or vapor produced by heating a liquid reaction agent. The device comprises a first container for receiving the object to be sterilized, a second container for receiving the liquid reaction agent and having a volume substantially smaller than the volume of the first container, means for interconnecting the interiors of the first and second containers to enable a flow of fluid and gases therebetween, and means for heating the liquid reaction agent in the second container to produce a hot gas for sterilizing the object in the first container. The means for heating includes a source of radiation which may be either infrared radiation or microwave radiation, means for creating an area of high energy density for the radiation, and means for positioning the second container in the area of the high energy density so that the liquid reaction agent in the second container is heated to a temperature to vaporize it into a hot gas which flows through the means for interconnecting to sterilize the objects in the first container.

The employment of a microwave radiator is particularly advantageous. For example, micro-organisms, which are not fluid filled per se such as for example organism creating or breeding spores, may not be killed by the microwave energy. However, the device, which uses microwave energy for heating a reaction agent to create steam or gas to sterilize the object will easily kill these micro-organisms or spore creating organisms. When microwave energy is directed on metal parts, it will form spark gaps at border surfaces and seams of the parts and these sparks will result in surface destruction of the object to be sterilized. In the device of the present invention which utilizes a microwave energy to heat a reaction agent to create steam which is conducted away from the microwave chamber, parts can be sterilized without the problems with spark gaps being formed. In addition, microwaves normally do not penetrate into cracks and thus will not kill micro-organisms which are situated therein. However, the heated gases created from heating the reaction agent will penetrate into seams and cracks to obtain the desired sterilization by killing micro-organisms located therein.

In the device of the present invention, the material to be sterilized is kept outside of the field covered by the source of radiation and these parts are thus only contacted by the steam or gases generated in the second container. If one keeps the first container, which accepts the object to be sterilized and forms the sterilization spaces, as small as possible and advantageously at a size, which corresponds to the acceptance of only one or a few objects to be sterilized, then the volume or amount of fluid required to generate the steam or gas is relatively small. With a relatively small amount or volume of fluid, extremely short heating times are achieved and also the cooling time is likewise shortened by the same degree.

Given a container size of approximately 50 ml for receiving the material to be sterilized, an amount or volume of liquid reaction agent of approximately 4 ml and a radiator power of approximately 500 watts, sterilization is possible in the few minutes by the device of the present invention. By means of selecting suitable reaction agents with various boiling points, a fast and secure sterilization which is matched to the particular material can be achieved.

When utilizing an infrared source, as a source of radiation, the means for concentrating the radiation is preferably an elliptical reflector having first and second focal lines and the second container is positioned in one of the first and second focal lines while the source of infrared radiation is placed at the other. In addition, at least the second container will be formed of a material which has a good infrared permeability for example glass. The elliptical reflector should be provided with a good reflective coating such as a gold coating and is manufactured as a thin wall of material with a low thermal capacity.

In either embodiment of the device, which uses either an infrared source of radiation or a microwave source, means for creating an explosive transfer of the reactive agent can be utilized. The means for explosive transfer will prevent movement of the vaporized reaction agent until the vapor pressure have reached a level in the range of 1.5 to 5 bars so that the liquid reaction agent will be heated until it exceeds this given vapor pressure at which time the means releases the vapor pressure to explosively flow into the first container. This means for creating an explosive transfer can be either a plastic-like bag which is designed to burst at a specific vapor pressure within the above-mentioned range or a partition film or seal which is disposed in the means for connecting to seal the two containers apart until the vapor pressure of the reaction agent in the second container reaches the specified level.

In addition, to aid in obtaining the penetration of the gas or vapor into the various seams and crevises of the object, the first container can be provided with means for creating a vacuum in a range of 1 to 200 Torr. The means include an inlet or connection having a valve which can be connected to a vacuum source so that both the first container and the object placed in the first container to be sterilized can be placed under a vacuum. This is particularly useful when using the explosive transfer process with either the breakable bag or breakable film or seal.

The first and second container can be separate containers or vessels which can be joined together by the means for interconnecting or can be formed as a single member or vessel which has a large portion that forms the first container and tapers into a second smaller diameter portion forming the second container. Thus, the vessel can have a bottle like shape with a bottle neck forming the second container which receives the reaction agent. If the containers are formed of two separate units, the means for interconnecting can include a releasable connection which allows assembly and disassembly of the two containers. In order to prevent the object being sterilized from entering the second container particularly if the two containers are interconnected with a rather large passageway, a screen or perforated element, which will prevent the object from entering this second container but enable both the draining of fluid and the passage of the hot vapor and gases, may be utilized.

BRIEF DESCRIPTION OF THE DRAWINGS

FIG. 3 is a cross-sectional view with portions in elevation for purposes of illustration of an embodiment of the device in accordance with the present invention;

FIG. 4 is a cross-sectional view of an embodiment of the interconnected containers in accordance with the present invention; and FIG. 5 is a perspective view of a bag containing a reaction agent in accordance with one embodiment of the invention.

DESCRIPTION OF THE PREFERRED EMBODIMENTS

Figure 1:
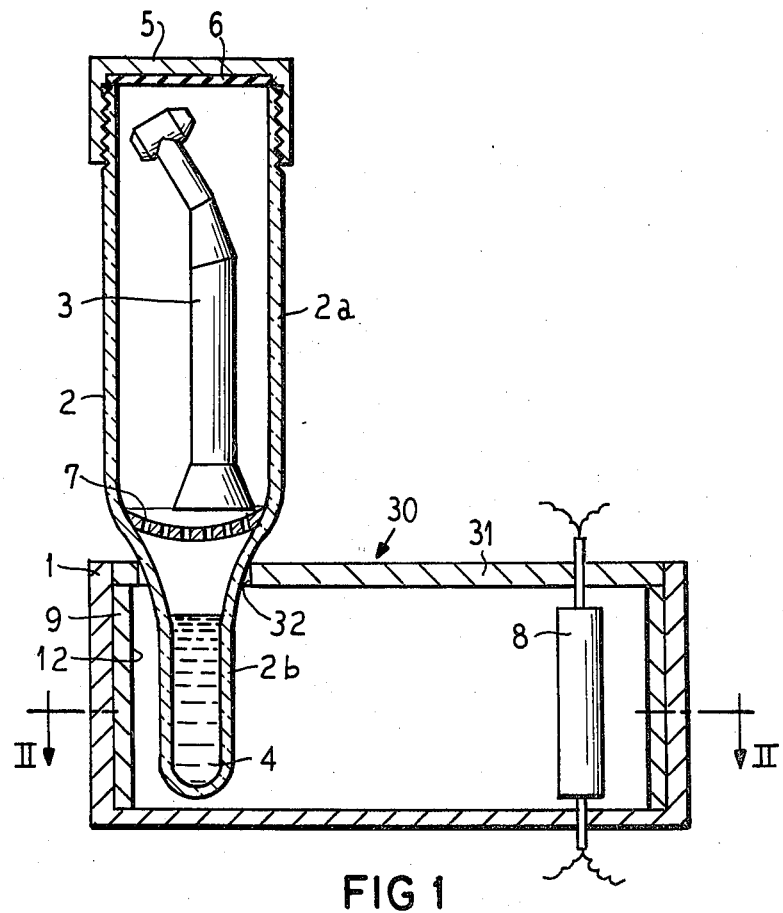
FIG. 1 is a cross-sectional view with portions in elevation of a device in accordance with the present invention.
Figure 2:
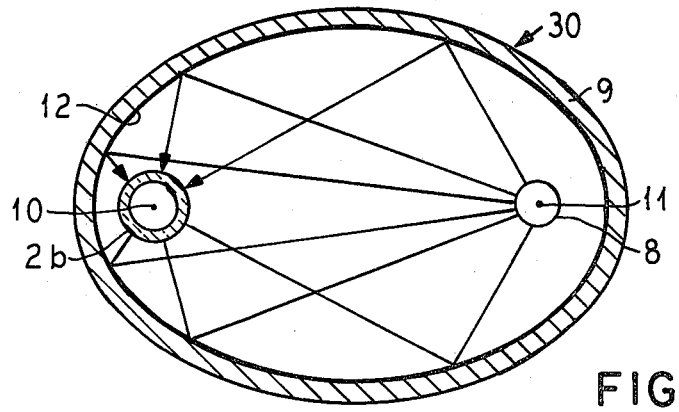
FIG. 2 is a cross-sectional view with portions removed for purposes of illustrations taken along the lines II—II of FIG. 1.

The principles of the present invention are particularly useful in a device generally indicated at 30 in FIGS. 1 and 2. The device 30 has a housing 1 and a removable container or vessel 2 which is illustrated as a bottle shape container or vessel which has a first large portion 2a forming a first container for accepting one or more objects to be sterilized for example a dental handpiece 3. The container or vessel 2 at one end tapers down into a second container section 2b of a small diameter which portion forms a second container for receiving a liquid reaction agent 4. As illustrated in the drawings, the container or vessel 2 has a bottle neck like portion which is closed at one end and forms the second container.

To enable access to the first container which is in the portion 2a of the vessel 2, the end adjacent the enlarged portion 2a has a cap or top 5 which is removable. As illustrate, the cap 5 has a seal 6 and is threaded or screwed onto the end of the portion 2a forming the first container. A portion of the vessel 2, which extends between the small second container 2b and the larger first container portion 2a, acts as means to communicate the interior of the two containers together and receives a perforated insert or screen 7 which will allow passage of fluids, steam or vapor. However, the insert 7 will prevent objects, particularly smaller objects which are to be sterilized from entering the lower container section such as 2b.

In the device 30, a source of radiation, which is in the form of a rod-shaped infrared radiator 8, is provided in the housing 1, which housings also has an elliptical reflector 9. The elliptical reflector 9 has a first focal line 10 (FIG. 2) and a second focal line 11. As best illustrated in FIG. 2, the rod-shaped infrared radiator 8 which has a cylindrical shape is positioned with its axis on the a second focal line 11 while the second container portion formed by the small portion 2b is positioned at the first focal line 10. In order to support the vessel 2 with the small portion 2b on the focal line 10, means for positioning which includes a lid 31 of the housing having an aperture 32, are utilized. Thus, the small end 2b of the vessel 2 is inserted through the aperture 32 to be positioned on one of the focal lines of the elliptical mirror 9. By being positioned on the focal point or line 10, a very high beam concentration of the infrared radiation as indicated by the few lines in FIG. 2 are focused and projected onto the container 2b and will cause a fast evaporation or boiling of the reaction agent to produce the hot steam or gas used for sterilizing.

Expediently, the height of the reflector 9 is approximately the same as the length of the container section 2b in which the reaction agent is provided. The reflector 9 advantageously consists of thin wall of material with a low thermal capacity and can, as indicated in the FIG. 1, be provided with a reflective coating 12 for example formed by a gold layer or coating. Advantageously, the length of the rod shaped infrared radiator 8 is only slightly smaller than the overall height of the reflector 9 so that the greatest possible field can be generated.

Given an assumed volume of the first container or chamber formed by the portion 2a for the object to be sterilized of approximately 50 ml, and a volume of approximately 4 ml for the second container formed by the section 2b, a radiator power of approximately 50 watts will be sufficient. Thus, the infrared radiator can be directly operated at line voltage. In order to achieve a conversion of the energy which is as lost free as possible, at least the portion 2b for the second container, which receives the reaction agent 4, should consist of a material with a good infrared permeability for example glass. Advantageously, the radiation of the infrared radiator 8 is spectrally matched to the absorption band of the reaction agent employed so that as viewed over the entire radiation range, the absorption and radiation intensity curves are approximately of equal coverage. Various liquids or liquid mixtures which exhibit a high infrared absorption for example, water and alcohol can be employed as the reaction agent.

An embodiment of the device is generally indicated at 30' in FIG. 3. In this embodiment, a microwave generator with a magnatron 13 is provided instead of an infrared radiator as the source of radiation. The magnatron 13 emits microwave radiation via a discharge nozzle 14 into a housing 15 which serves as a cavity resonator. In the area of the highest power density which is empirically determined, the cavity resonator is provided with means for positioning the second container such as the section or portion 2b. This means for positioning is illustrated as being a bore 16 with a diameter of approximately 8 to 10 mm in an upper wall of the housing 15. Thus, the container or vessel 2 is supported in the housing 15 in an easily removable fashion. Under the influence of the microwave energy, the reaction agent 4 in the second container 2b will boil and is converted into a vapor or gas phase. The agent will condense on the inside wall of the vessel 2 and on the object to be sterilized and then finally drain back into the portion 2b.

The housing 15 can exhibit a plurality of openings 16 for the acceptance of a plurality of the containers 2 so that the plurality of containers can be simultaneously heated or charged. It should be noted, that each of the bores 16 can be provided with a seal arrangement which will close the bore when the vessels such as 2 is not inserted therein. The container 2 can be designed in such a manner that it serves as a storage container, and, it is also conceivable to secure it stationarily into the housing. Then the material or object, which is to be sterilized can be inserted into a gas permeable foil tube which after being sewn shut is then inserted into the fixed container.

If the first container has volume of 50 ml, the power of the magnatron can amount to approximately 500 watts. The circuit for the magnatron can be advantageously designed in such a manner that the power output will be reduced for example to a half power output after complete evaporation of the reaction agent has been obtained. The circuit can use either a photoelectrical sampling or a vapor pressure measurement to determine when all of agent has been vaporized.

Another advantageous embodiment of the vessel which accepts the object to be sterilized and also has a section for receiving the reaction fluid 4 is shown in FIG. 4 and is the vessel or unit 2'. The container or vessel 2' has sections 2a' and 2b' which are connected to one another via a screw type connections 17 which would be in the narrow tapered portion. A partition film 18 or seal is disposed between the two portions and held by the screw-type connection. The material of the partition film or seal is selected in such a manner that the film will burst given a specific vapor pressure. As a rule, this pressure will be selected to fall in a range of 1.5 to 5 bars. When the vapor pressure in the portion 2b' reaches this specific value, the seal or film 18 will break and allow an explosive spread of the vapor or gas into the first container section 2a', which contains the instrument 3 for sterilization. A significant advantage of this solution is that the extremely short but very powerful charging with a very high kinetic energy is given by means of which as tests have shown a particularly good germ killing effect. Instead of filling the reaction fluid 4 into a container section such as 2b', the reaction agent can be packaged in a bag 19 (FIG. 5) which contains a uniform portion. The bag 19 will consist of a transparent plastic and has a volume in a range of 2 through 10 cm$^3$ and approximately 60% of the volume of the bag is filled with the fluid 4. Expediently the bag is sealed shut. When the bag is inserted into a lower section such as 2b' before the two sections 2a' and 2b' are screwed together, then upon heating either with a microwave source or by infrared radiation, the fluid in the bag will be transformed into a gas of a pressure reaching a specific mount falling in the range of 1.5 to 5 bars prior to the bag bursting open. Again as in the case with the breakable seal 18, an explosive spread of the heated gases and vapors with a very high kinetic energy is obtained. Thus the seal 18 and the bag 19 form means for explosively transferring the hot gases from the second container to the first container.

Sterilization is particularly effective if after placing the objects such as the dental handpiece 3 in the first container such as formed by the portion 2a', the first container is evacuated to a range of 1 to 200 Torr. This can occur if the upper portion 2a' forming the first container is provided with a modified lid 5' which has a connection 20 for a line 21 that extends to a vacuum system. The connection 20 is also provided with a check valve arrangement such as the ball 22 which will maintain the vacuum in the container space after removal of the line 21 from the connection 20. A satisfactory source or vacuum system for evacuating the upper chamber or portion 2a is by means of a water jet or air jet vacuum pump. By placing the upper container in a vacuum, gases that may be entrapped in various seams and prevent penetration of the heated vapor or gas will be removed. When utilizing the above described explosion transfer of the vapor or gas at a specific vapor pressure, the presence of the vacuum in the upper container portion 2a' will greatly intensify the sterilization effect. This is particularly true because the explosive spreading of the vapor is drawn into practically any small space due to the previously existing vacuum.

Because of the space saving construction, the device 30 or 30' can be employed anywhere in a medical practice. For example, it can be used in bacteriological, hygenic or chemical laboratories. In particular, an advantageous application is in the dental practice to enable sterilizing dental handpieces without subjecting the dental handpiece or the instruments to direct bombardment by the radiant energy such as microwaves.

Although various minor modifications may be suggested by those versed in the art, it should be understood that I wish to embody within the scope of the patent granted hereon, all such modifications as reasonably and properly come within the scope of my contribution to the art.

I claim:

1. A device for sterilizing medical and dental objects, such as instruments and the like, by contacting the object with a gas produced by heating a liquid reaction agent, said device comprising a single vessel having an enlarged portion forming a first container for receiving the object to be sterilized, a narrow portion forming a second container for receiving said liquid reaction agent and having a volume substantially smaller than the volume of the first container and a connecting portion forming means for interconnecting the interiors of said first and second containers to enable flow of fluid and gases therebetween; and means for heating the liquid reaction agent in the second container to produce a hot gas for sterilizing each object in the first container, said means for heating including a source of radiation, means for creating an area of high energy density for the radiation, and means for positioning the second container in the area of high energy density so that the liquid reaction agent in the second container is heated to a temperature to vaporize it into a hot gas, which flows through the means for interconnecting to sterilize each object in the first container.

2. A device according to claim 1, wherein the connecting portion is a tapering portion of the vessel extending between the enlarged portion and the narrow portion.

3. A device according to claim 2, wherein said vessel has a bottle-like shape wherein a bottle neck portion forms the second container for accepting the liquid reaction agent.

4. A device according to claim 2, which includes a porous screen element disposed in the vessel adjacent the tapering portion to prevent each object being sterilized from entering into the second container.

5. A device according to claim 3, wherein said means for positioning removably supports the vessel in a housing of the source of radiation with the second container in the desired position.

6. A device according to claim 5, wherein the means for positioning comprises a plurality of openings in a cover of the housing with each of said openings receiving a separate second container of the vessel for positioning on said housing.

7. A device according to claim 3, wherein the first container is essentially designed for the acceptance of only one hand instrument.

8. A device according to claim 1, wherein the first container includes means enabling evacuation of the interior of said first container to a vacuum in the range of 1 to 200 Torr, said means for enabling evacuation comprising said first container having a connection to enable interconnecting the interior of the first container to a vacuum system.

9. A device for sterilizing medical and dental objects, such as instruments and the like, by contacting the object with a gas produced by heating a liquid reaction agent, said device comprising a first container for receiving the object to be sterilized; a second container for receiving said liquid reaction agent and having a volume substantially smaller than the volume of the first container; means for interconnecting the interiors of said first and second containers to enable flow of fluid and gases therebetween; and means for heating the liquid reaction agent in the second container to produce a hot gas for sterilizing each object in the first container, said means for heating including an infrared radiator means for creating an area of high energy density for the infrared radiation including an elliptical reflector having a pair of focal lines with the infrared radiator being disposed at one of said pair of focal lines, and means for positioning the second container in the area of high energy density at the other of said pair of focal lines so that the liquid reaction agent in the second container is heated to a temperature to vaporize it into a hot gas, which flows through the means for interconnecting to sterilize each object in the first container.

10. A device according to claim 9, wherein the reflector has an overall height which at least corresponds to the overall height of the second container.

11. A device according to claim 9, wherein the inside surface of the reflector is provided with a good reflective coating.

12. A device according to claim 11, wherein said reflective coating is a gold coating.

13. A device according to claim 9, wherein the reflector is manufactured of a thin wall material with a low thermal capacity.

14. A device to claim 9, wherein at least the second container consists of material with a good infrared permeability.

15. A device according to claim 9, wherein the liquid reaction agent consists of a fluid selected from a group of fluids and fluid mixtures exhibiting high infrared absorption.

16. A device according to claim 15, wherein the radiation of the infrared radiator and the absorption band of the reaction agent are spectrally matched.

17. A device according to claim 9, wherein the infrared radiator is designed as a rod shape having an axis lying substantially on said focal line.

18. A device for sterilizing medical and dental objects, such as instruments and the like, by contacting the object with a heated gas produced by heating a liquid reaction agent, said device comprising a first container for receiving the object to be sterilized; a second container for receiving said liquid reaction agent and having a volume substantially smaller than the volume of the first container; means for interconnecting the interiors of said first and second containers to enable flow of fluid and gases therebetween; and means for heating the liquid reaction agent in the second container to produce a hot gas for sterilizing each object in the first container, said means for heating including a source of radiation, means for creating an area of high energy density for the radiation, and means for positioning the second container in the area of high energy density, said second container including means for explosively transferring the heated gas of the heated reaction agent from said second container into said first container, said means for explosively transferring preventing flow of the vaporized gases until a predetermined pressure in a range of 1.5 to 5 bars is reached, so that the liquid reaction agent in the second container is heated to a temperature to vaporize it into a hot gas of a predetermined pressure and is then released to flow through the means for interconnecting to sterilize each object in the first container.

19. A device according to claim 18, wherein the means for an explosive transfer comprises a bag sealably receiving the liquid reaction agent, said bag being designed to burst at a specific vapor pressure falling in the range of 1.5 to 5 bars so that an explosive transfer of the gaseous reaction agent into the first container occurs after breaking of said bag.

20. A device according to claim 19, wherein the first container includes means enabling evacuation of the first container to a vacuum in a range of 1 to 200 Torr, said means for enabling evacuation including a connection disposed on the first container to enable connection of the interior of the first container to a vacuum system.

21. A device according to claim 18, wherein the means for interconnecting the first and second containers, releasably connects said containers together, said means for explosive transfer of the reaction agent including a breakable seal received by the means for interconnecting to isolate the first container from the second container, said seal breaking at a predetermined vapor pressure in the range of 1.5 to 5 bars so that the vaporized reaction agent in the second container must reach a predetermined vapor pressure prior to breaking the seal to enter into the first container to sterilize an object therein.

22. A device according to claim 21, wherein the first container includes means enabling evacuation of the container to a vacuum in a range of 1 to 200 Torr, said means for enabling evacuation including a connection disposed on said first container to enable connection of the interior of the first container to a vacuum system.

23. A device for sterilizing medical and dental objects, such as instruments and the like, by contacting the object with a gas produced by heating a liquid reaction agent, said device comprising a first container for receiving the object to be sterilized; a second container for receiving said liquid reaction agent and having a volume substantially smaller than the volume of the first container; means for interconnecting the interiors of said first and second containers to enable flow of fluid and gases therebetween; and means for heating the liquid reaction agent in the second container to produce a hot gas for sterilizing each object in the first container, said means for heating including a microwave generator having a discharge nozzle for discharging microwave radiation into a cavity resonator in a housing, means for creating an area of high energy density for the microwave radiation being formed by said cavity resonator, and means for positioning the second container in the area of high energy density comprising an opening in the housing for receiving and supporting the second container in the desired position in said housing while the first container with the part to be sterilized is disposed outside of said housing, so that the liquid reaction agent in the second container is heated to a temperature to vaporize it into a hot gas, which flows through the means for interconnecting to sterilize each object in the first container.

* * * * *